US007069552B2

United States Patent
Lindberg et al.

(10) Patent No.: US 7,069,552 B2
(45) Date of Patent: Jun. 27, 2006

(54) METHOD FOR PROVIDING SOFTWARE TO AN IMPLANTABLE MEDICAL DEVICE SYSTEM

(75) Inventors: Magnus Lindberg, Sundbyberg (SE); Hans Abrahamson, Stockholm (SE); Mats Arturson, Täby (SE)

(73) Assignee: St. Jude Medical AB, Jarfalla (SE)

( * ) Notice: Subject to any disclaimer, the term of this patent is extended or adjusted under 35 U.S.C. 154(b) by 583 days.

(21) Appl. No.: 10/153,579

(22) Filed: May 22, 2002

(65) Prior Publication Data

US 2003/0046677 A1    Mar. 6, 2003

(30) Foreign Application Priority Data

Aug. 30, 2001    (SE) .................................... 0102918

(51) Int. Cl.
*G06F 9/44* (2006.01)
(52) U.S. Cl. ....................... 717/173; 717/122; 717/170
(58) Field of Classification Search ........ 717/168–178, 717/120–122; 607/30
See application file for complete search history.

(56) References Cited

U.S. PATENT DOCUMENTS

| | | | | |
|---|---|---|---|---|
| 4,558,413 A | * | 12/1985 | Schmidt et al. ............. | 707/203 |
| 4,809,697 A | | 3/1989 | Causey, III et al. .......... | 607/31 |
| 5,182,553 A | | 1/1993 | Kung .......................... | 340/7.1 |
| 5,456,691 A | | 10/1995 | Snell ............................ | 607/30 |
| 5,456,692 A | | 10/1995 | Smith, Jr. et al. ............. | 607/31 |
| 5,528,490 A | * | 6/1996 | Hill ............................. | 717/168 |
| 5,690,690 A | | 11/1997 | Nappholz et al. ............. | 607/30 |
| 5,800,473 A | | 9/1998 | Faisandier .................... | 607/59 |
| 5,843,138 A | | 12/1998 | Evers et al. .................. | 607/30 |
| 6,006,034 A | * | 12/1999 | Heath et al. ................. | 717/170 |
| 6,083,248 A | | 7/2000 | Thompson .................... | 607/30 |
| 6,088,618 A | | 7/2000 | Kerver ......................... | 607/30 |
| 6,157,859 A | | 12/2000 | Alt ............................... | 607/4 |
| 6,167,567 A | * | 12/2000 | Chiles et al. ................ | 717/173 |
| 6,199,204 B1 | * | 3/2001 | Donohue ..................... | 717/178 |
| 6,205,579 B1 | * | 3/2001 | Southgate .................... | 717/173 |
| 6,363,282 B1 | | 3/2002 | Nichols et al. ............... | 607/30 |
| 6,718,547 B1 | * | 4/2004 | Takeo .......................... | 717/170 |

FOREIGN PATENT DOCUMENTS

| | | |
|---|---|---|
| WO | WO 01/48675 | 7/2001 |
| WO | WO 01/52934 | 7/2001 |

* cited by examiner

*Primary Examiner*—Ted T. Vo
(74) *Attorney, Agent, or Firm*—Schiff Hardin LLP

(57) ABSTRACT

In a method for providing software to an implantable medical device system, including an implanted medical device and a presentation unit in communication with each other, a most current version of software for operating one or more of these system units is stored at a server which is remote from the implanted medical device system. Upon each start-up of the presentation unit, a communication link is established between the server and the presentation unit, and information is provided from the presentation unit to the server identifying the software which is respectively currently stored in one or more of the system units. The server determines whether the currently stored software in the system units requires an update and, if so, the server downloads the software version stored at the server to any of the system units which is/are in need of updated software.

11 Claims, 5 Drawing Sheets

METHOD FOR PROVIDING SOFTWARE TO AN IMPLANTABLE MEDICAL DEVICE SYSTEM

BACKGROUND OF THE INVENTION

1. Field of the Invention

The present invention is directed to a method for providing software, such as updated software or corrected software, to an implantable medical device system, of the type having an implantable medical device (IMD) and a presentation unit (PU).

2. Description of the Prior Art

Implantable medical device systems are currently available from a number of manufacturers. The details of the components of these various implantable medical device systems vary from manufacturer to manufacturer, however, most implantable medical device systems include the basic components of an implantable medical device (IMD) and a programmer or presentation unit (PU). One or both of these basic components is operable according to one or more software programs. The operating software program for each component is stored in that component.

It is almost certain that updated software or corrected software will become available for an implantable medical device system which is in use for any significant length of time. This means that the software currently stored in the components of the implantable medical device system must be replaced. This is currently accomplished by delivering the updated or corrected software to every programmer in the field, which is not only a time-consuming procedure in itself, but also results in an unavoidable delay in the updated or corrected software being physically present at the programmer after the time at which the updated or corrected software is created.

Additionally, this current procedure poses significant problems for clinics and hospitals, which use a number of different models of implantable medical device systems from each manufacturer. This requires the hospital or clinic to maintain a different programmer for each of these different models, and each time updated or corrected software becomes available for that model, the correct programmers must be identified for software replacement, and the delivered software must then be entered into the programmer. The updated or corrected software may alter not only the operation of the programmer, but also the operation of the implanted medical device. If the operation of the implantable medical device is altered by the updated or corrected software, then the programmer, with the updated or corrected software installed therein, must be placed in communication with each implanted medical device in the field which is in need of updated or corrected software. If the implanted medical device system does not include the feature of allowing remote communication between the implanted medical device and the programmer, this means that the patient in whom the implanted medical device is implanted must make a visit to the hospital or clinic so that the implanted medical device and the programmer can be placed in communication to download the updated or corrected software to the implanted medical device. If the correction or update is sufficiently important, this may require a special visit by the patient to the hospital or clinic. In other cases, the download of software to the implantable medical device will take place at the patient's next routine visit to the hospital or clinic, but this results in a further delay with respect to the actual installation of the updated or corrected software in the implantable medical device.

SUMMARY OF THE INVENTION

It is an object of the present invention to provide a method for providing software to an implanted medical device system which allows updated or corrected software to be installed in the implanted medical device system in a manner which is more easily manageable than current procedures, and which minimizes delays in installing the updated or corrected software in the implantable medical device system.

The above object is achieved in accordance with the principles of the present invention in a method for providing software to an implantable medical device system, having an implantable medical device and a presentation unit, wherein software, such as updated or corrected software, for operating the components of the implanted medical device system is stored at a server which is remote from the implanted medical device system. At each start-up of the presentation unit, a communication link is established between the server and the presentation unit. At the server, a determination is made whether the presentation unit in communication with the server, and/or another unit in the system, is in need of replacement software, by virtue of the unit containing an out-of-date version of the operating software, for which an updated or corrected version is stored at the server. If the system unit is in fact in need of replacement software, the updated or corrected software stored at the server is downloaded to the system unit via the aforementioned communication link.

The communication link between the implanted medical device system and the server can ensue in different ways. A person associated with the implanted medical device system, such as the patient or attending physician, can periodically establish communication with the server for the specific purpose of obtaining the latest software version, if a later software version than the currently installed version exists. Alternatively, when a routine communication with the server is established for any sort of task, the server can interrogate the implantable medical device system to determine if a software replacement is needed.

At least for software for operating the presentation unit (programmer) the software need not be permanently stored in the presentation unit. Every time the presentation unit is activated, a communication with the server can be established and whatever software is stored at the server for designated task will then be automatically downloaded to the presentation unit for use by the presentation unit in conducting the current procedure. Since the server will always contain the most recent version of the operating software, it is insured that the programmer will always operate with this most recent version. When communication between the programming unit and the server is established, a handshake procedure can be initiated whereby the server identifies all relevant information regarding the presentation unit, such as its model number, the type of user (i.e.: patient or physician or nurse), time and date of last use, etc. Based on this information, the most appropriate software is downloaded to the presentation unit. The downloaded software, therefore, can be specifically adapted, for example, dependent on whether the user is a physician or a patient.

In a further embodiment, the software is downloaded from the server and is permanently stored in the programmer or in the implanted medical device. ("Permanent storage" as used herein means storage of software in a manner which is retained for subsequent use by the system unit, but still allows for replacement of the software if and when updated or corrected software becomes available.) In this embodiment, in addition to the server interrogating the presentation unit or the implanted medical device with regard to the aforementioned information, the interrogation also includes an identification of the software currently installed in the unit, so that the server can determine whether the unit does, in fact, have the latest version, or is in need of a software replacement. The server can communicate directly with the implanted medical device for this purpose, or can communicate with the implanted medical device through a further communication link between the presentation unit and the implanted medical device.

In a further embodiment of the inventive method, the software can be "distributed" among the different components of the implanted medical device system, with the server interrogating each of the software-operated units of the implanted medical device system when a communication link is established between the system and the server. In this embodiment, for example, different software programs can be downloaded to the implanted medical device and the presentation unit, respectively.

Each of the embodiments can have an emergency subroutine whereby, when communication between the presentation unit and the IMD is established, the aforementioned communication with the server is omitted, so that the implanted medical device can respond to the emergency in the quickest manner, without waiting for any software download.

DESCRIPTION OF THE PREFERRED EMBODIMENTS

Figure 1:
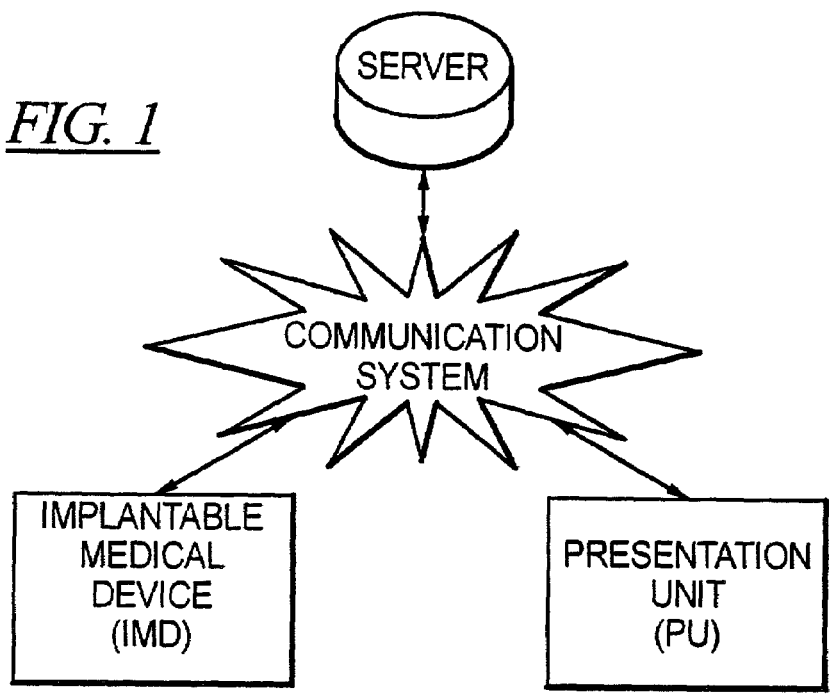
FIG. 1 is a schematic illustration of the basic components of an implantable medical device system, a communication system and a server for implementing the inventive method.

FIG. 1 shows the basic components for implementing the inventive method. These components include an implantable medical device system which includes at least an implantable medical device IMD and a presentation unit PU. A server is also provided, at which the latest version of software for operating the IMD and/or the PU is stored. The software stored at the server may be, for example, an updated version or a corrected version of the software currently installed in the IMD and/or the PU.

The server is able to communicate at least with the PU via a communication system. The communication system may be, for example, the internet, a telephone connection via modems, some other type of hardwired system, a radio communication system, etc. If the IMD is provided with features for linking the IMD to an external communication system, the server can communicate directly through this external communication system with the IMD.

The PU will also be in communication with the IMD by means of any standard arrangement, such as a coil or wand which is brought into proximity with the implanted medical device. All communication among the server, the PU and the IMD, in any combination and in any direction, are intended to be schematically indicated by the communication system in FIG. 1.

Figure 2:
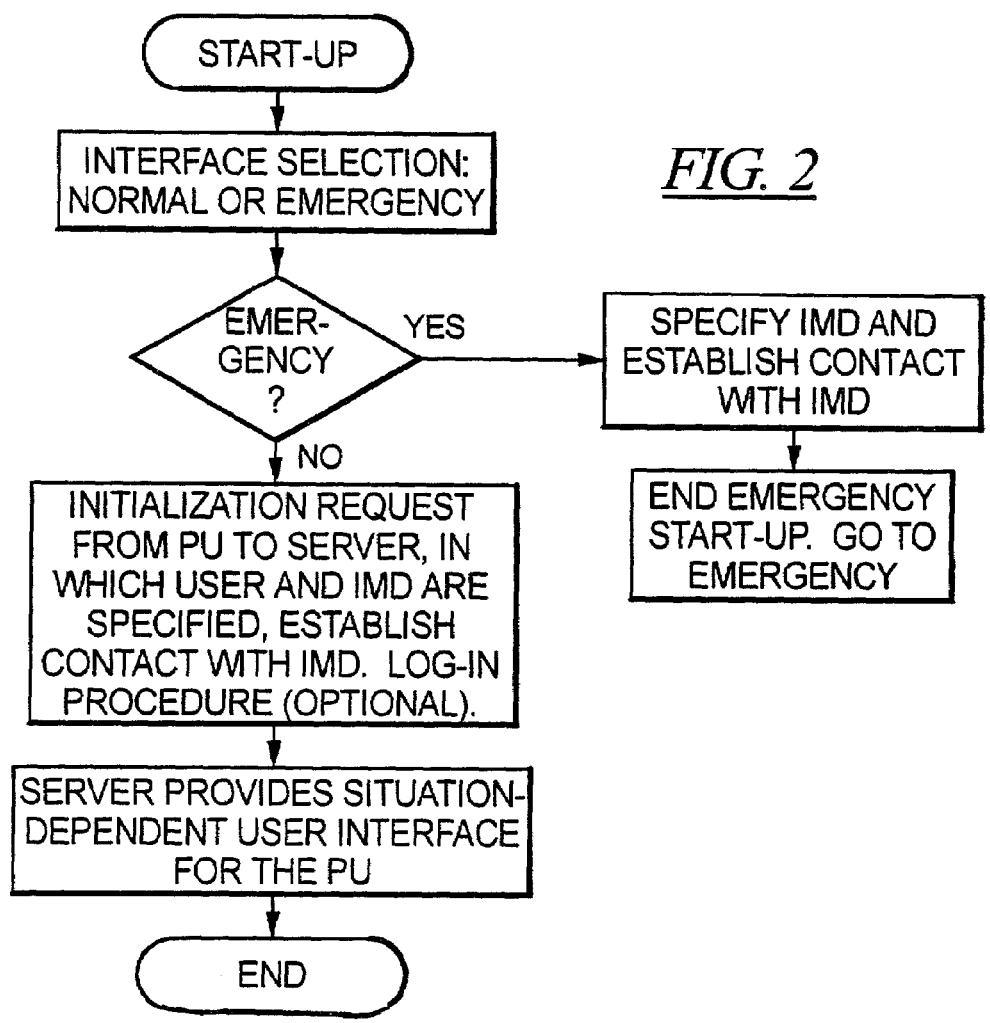
FIG. 2 is a flowchart for a first embodiment of the inventive method.

FIG. 2 is a flowchart for an embodiment of the invention wherein the software used for a particular request or task at the presentation unit PU is obtained from the server every time there is a start-up of the presentation unit PU.

As shown in FIG. 2, upon start-up, a selection is offered to the operator via an interface of the presentation unit PU, which allows the user to indicate whether operation is to proceed in a normal manner, or whether an emergency exists. The entry made by the user is interrogated, and if an emergency situation has been indicated, the implanted medical device IMD for which the emergency situation exists is specified, and a contact between the presentation unit PU and that implantable medical device is established. This ends the emergency start-up, and the emergency routine continues as explained below with regard to FIG. 8.

If the interrogation of the user entry indicates that normal operation is to proceed, an initialization request proceeds from the presentation unit PU to the server, wherein the user and the implanted medical device IMD are specified. Communication contact is also established between the presentation unit PU and the implanted medical device IMD. An optionally log-in procedure can be executed.

Based on the information provided to it by the presentation unit PU, the server then provides a situation-dependent user interface for the presentation unit PU.

This procedure is similar to techniques for a web-browser, wherein the content to be shown at the web-client is retrieved from a server, and any executable file is also provided by the server, and is subsequently run at the web-client. In the case of the inventive IMD system, the aforementioned situation-dependent user interface is retrieved from one or more servers.

As an example of this embodiment, a physician may be interfacing the IMD system using a hand-held unit. At start-up of the session, the doctor specifies which patient to interrogate, and contact is established between the implanted medical device IMD and the presentation unit PU. The menus and other display information which are shown at the presentation device PU for the physician are adjusted (matched) to the type of presentation unit PU which is being employed, and the type of implantable medical device IMD, by downloading software from the server. By making a selectable menu choice, a request is sent to the implantable medical device IMD, which initiates a software download from the implanted medical device IMD to the server, either directly or via the presentation unit PU. The software is executed in the implanted medical device IMD, and insures that proper information is sent to the presentation unit PU and made available for the physician.

Figure 3:
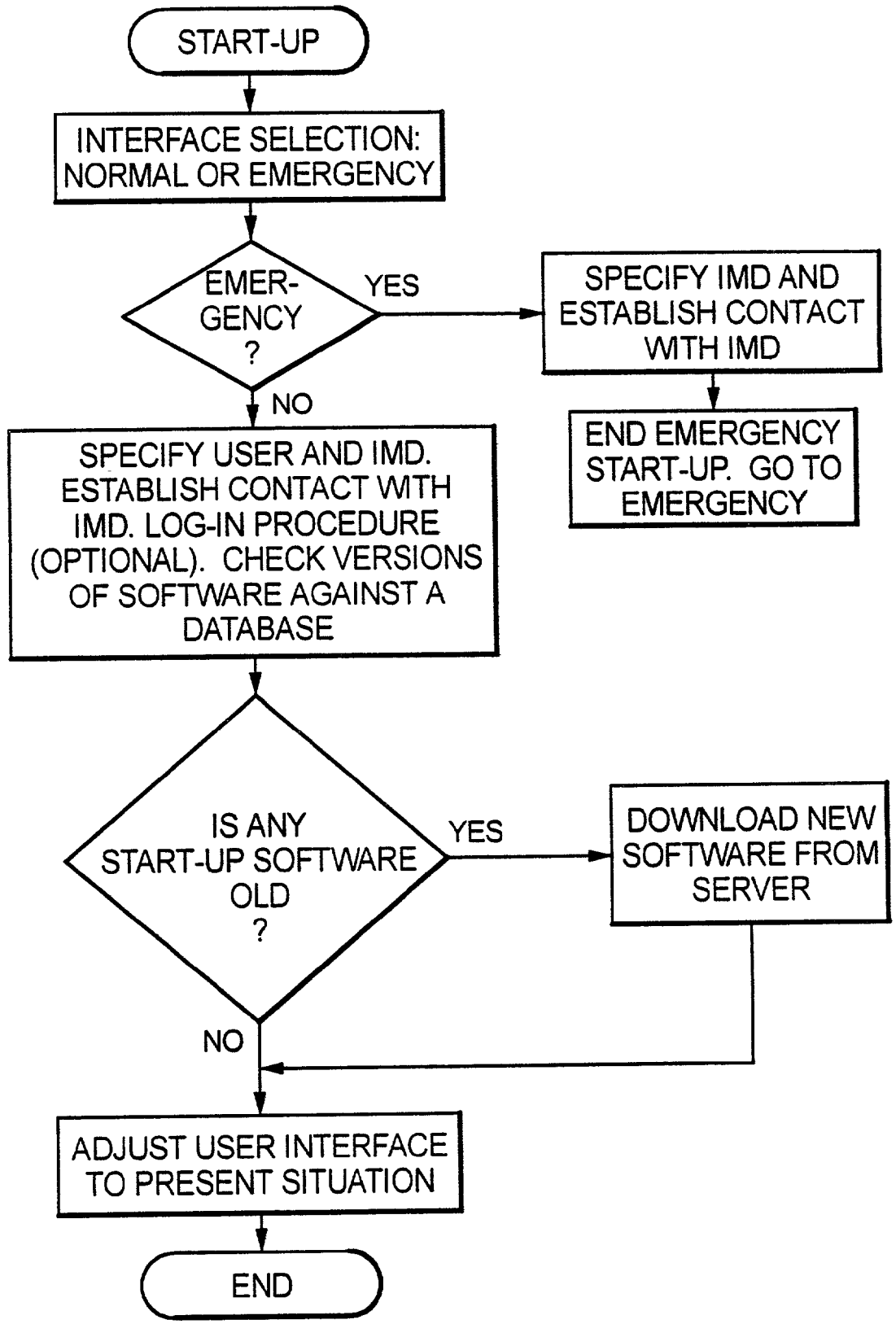
FIG. 3 is a flowchart for a second embodiment of the inventive method.

A further embodiment is shown in FIG. 3, wherein the procedure through the emergency interrogation is the same as described above in connection with the embodiment of FIG. 2. In the embodiment of FIG. 3, if no emergency situation exists, the user and the implanted medical device IMD are again specified, and communication contact is established between the presentation unit PU and the implantable medical device IMD, again with the optional use of a log-in procedure. In this embodiment, the software is distributed among the different units in the IMD system, at least between the presentation unit PU and the implanted medical device IMD. All versions of the software in all devices are checked against a database stored at the server to determine whether a new or corrected version-of any of the stored software exists. If so, the new or corrected software is downloaded from the case of the inventive IMD system, the aforementioned situation-dependent user interface is retrieved from one or more servers.

As an example of this embodiment, a physician may be interfacing the IMD system using a hand-held unit. At start-up of the session, the doctor specifies which patient to interrogate, and contact is established between the implanted medical device IMD and the presentation unit PU. The menus and other display information which are shown at the presentation device PU for the physician are adjusted (matched) to the type of presentation unit PU which is being employed, and the type of implantable medical device IMD, by downloading software from the server. By making a selectable menu choice, a request is sent to the implantable medical device IMD, which initiates a software download from the implanted medical device IMD to the server, either directly or via the presentation unit PU. The software is executed in the implanted medical device IMD, and insures that proper information is sent to the presentation unit PU and made available for the physician.

A further embodiment is shown in FIG. 3, wherein the procedure through the emergency interrogation is the same as described above in connection with the embodiment of FIG. 2. In the embodiment of FIG. 3, if no emergency situation exists, the user and the implanted medical device IMD are again specified, and communication contact is established between the presentation unit PU and the implantable medical device IMD, again with the optional use of a log-in procedure. In this embodiment, the software is distributed among the different units in the IMD system, at least between the presentation unit PU and the implanted medical device IMD. All versions of the software in all devices are checked against a database stored at the server to determine whether a new or corrected version of any of the stored software exists. If so, the new or corrected software is downloaded from the server and is supplied to the appropriate device. If the presentation unit PU is in need of updated software, the updated software can be downloaded directly from the server to the presentation unit PU. If it is the implanted medical device IMD that is in need of updated software, the downloading of the new software from the server can ensue directly to the implanted medical device IMD, if it has the capability of direct communication with the server or through the presentation unit PU. Again, the user interface is adjusted or adapted to reflect the present situation. The start-up routine is then ended.

Figure 4:
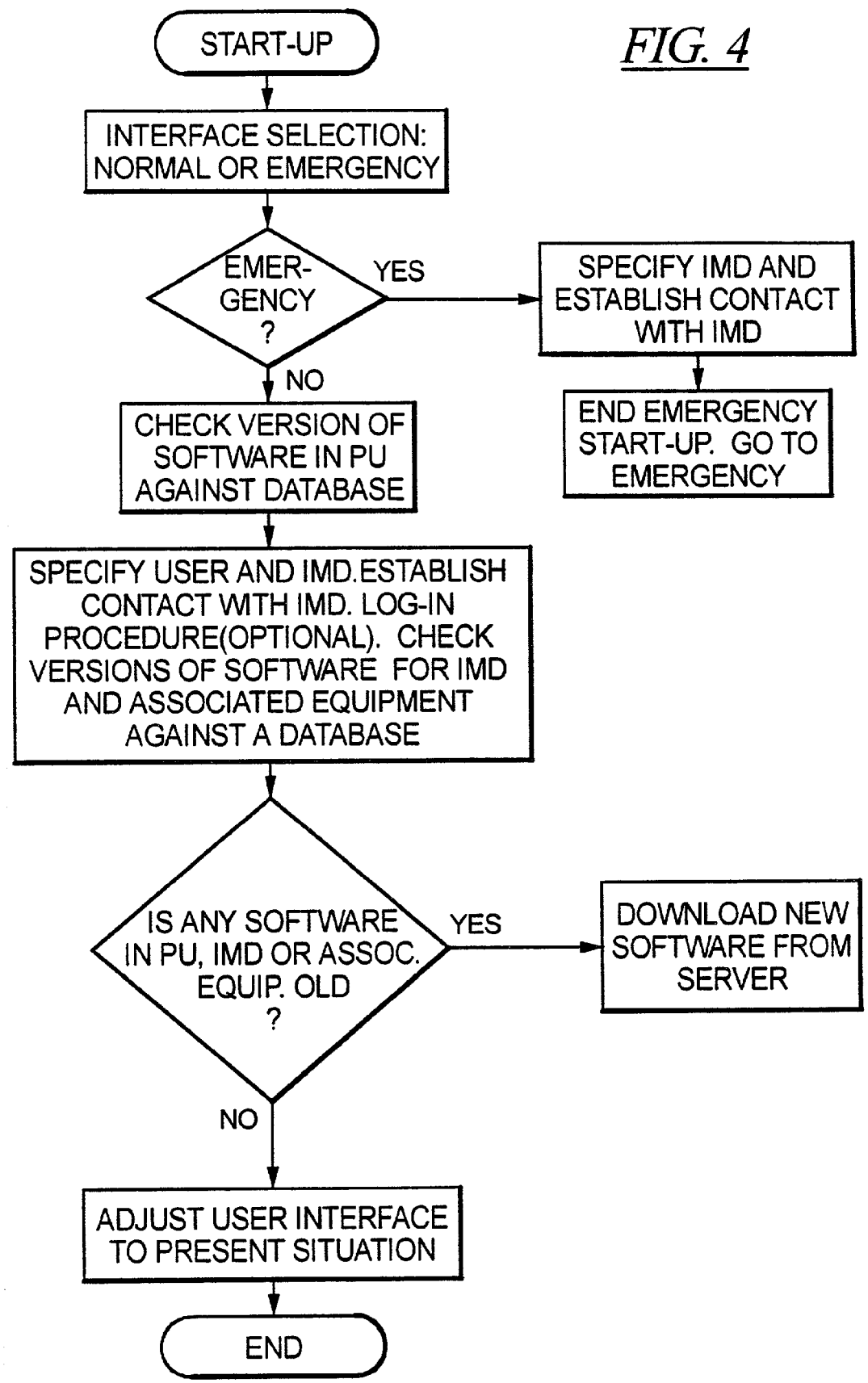
FIG. 4 is a flowchart for a third embodiment of the inventive method.

In the embodiment of FIG. 4, the determination of whether an emergency situation exists proceed as described above. In this embodiment, an identification of all versions of software stored in all of the components of the IMD system are stored in the presentation unit PU, and these are checked against a database at the server upon start-up. In this embodiment, communication proceeds only between the server and the presentation unit, which, in turn, communicates with the other components, such as the implanted medical device and any other associated equipment which may be present. Again, if updated or corrected software exists for the presentation unit PU or any other components of the IMD system, the server downloads the updated software to the presentation unit PU, and the presentation unit PU either uses the updated software itself or supplies it to the appropriate component. Again, the user interface is adjusted dependent on the present situation.

Alternatively, the check as to whether updated or corrected software is required can ensue on an "as needed" basis for each routine or task performed by the IMD system. When a particular task is undertaken or a particular routine is executed, the aforementioned check is made only for that routine or only for that task. Thus, unless and until a particular task or routine is executed, downloading of new software, specific for that task or routine, does not occur. Downloading thus occurs on a task-by-task or routine-by routine basis.

Figure 5:
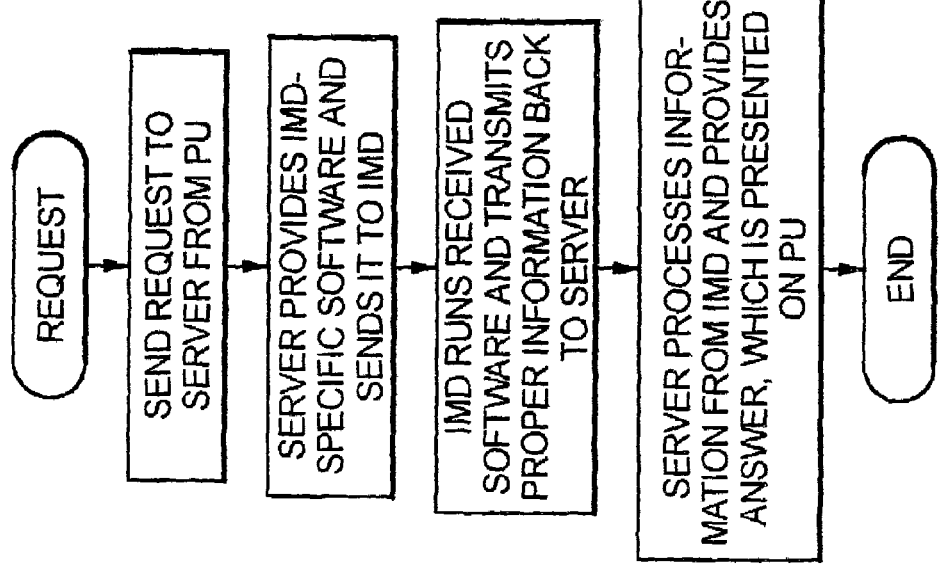
FIG. 5 is a flowchart for a request routine in the first embodiment of the inventive method.

FIG. 5 is a flowchart showing details of the request procedure for the embodiment of FIG. 2. A request is sent from the presentation unit PU to the server, and the server provides software which is specific for the specified implanted medical device IMD, and transmits the software to the IMD. The transmitted software is then run in the implanted medical device IMD after reception, and appropriate answer-back information is sent from the implanted medical device to the server. The server processes the answer-back information from the implanted medical device IMD, and provides an appropriate response, which is shown on the presentation unit PU.

Figure 6:
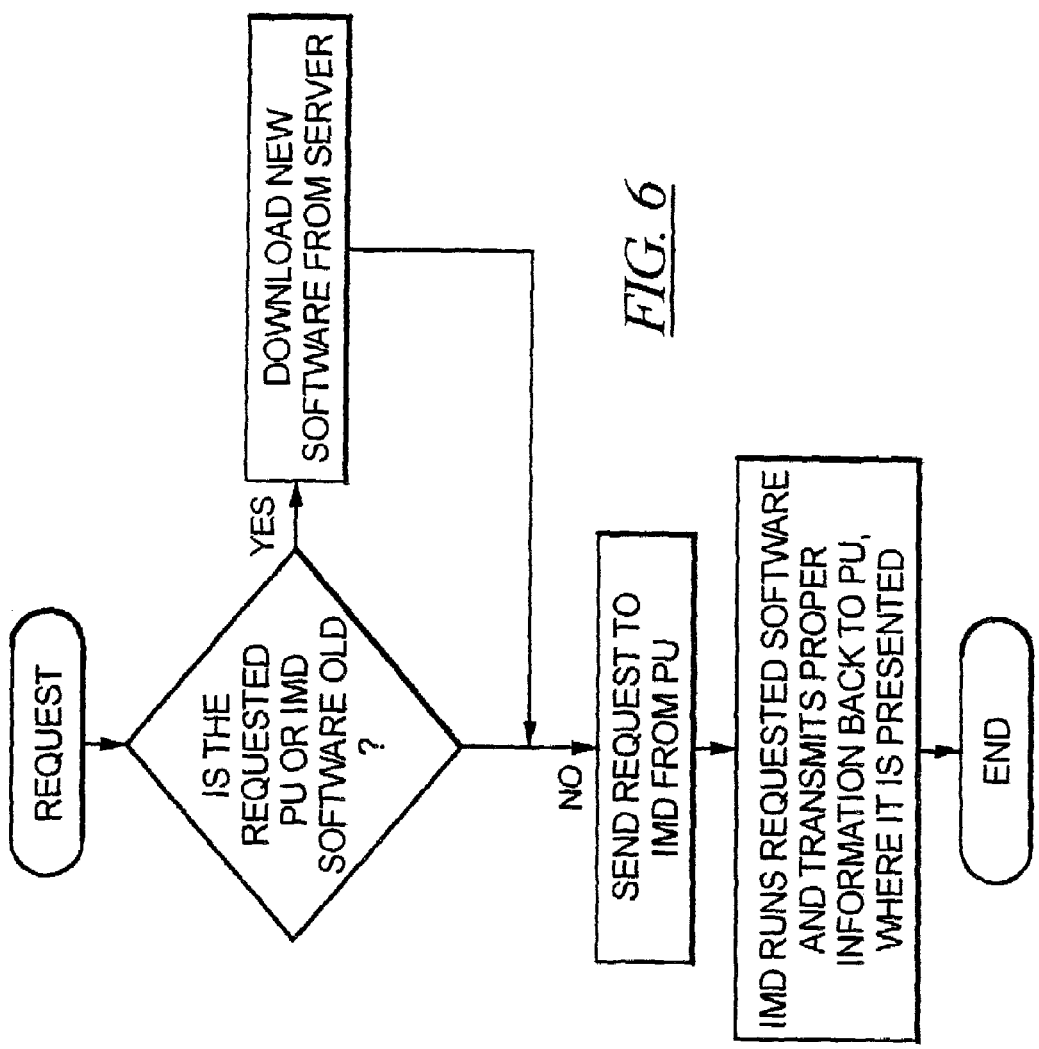
FIG. 6 is a flowchart for the request routine in the second embodiment of the inventive method.

The request procedure for the embodiment of FIG. 3 is shown in FIG. 6, the server determines whether the software requested by the presentation unit PU and/or the implanted medical device IMD is out-of-date, and if so, the current software served in the server is downloaded. If new software was entered into the implanted medical device IMD, the implanted medical device IMD then runs the requested software and transmits information back to the presentation unit PU, where it is displayed.

Figure 7:
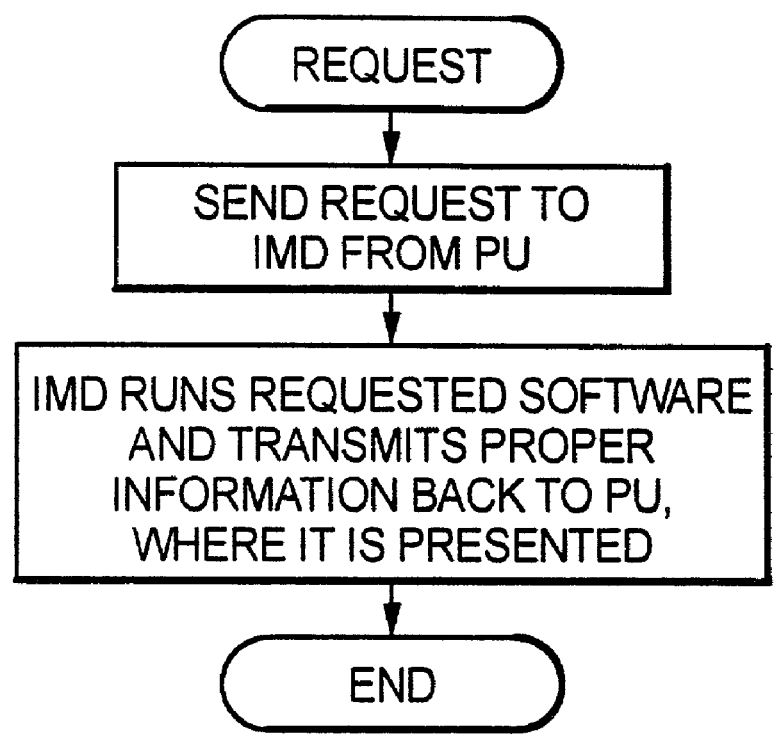
FIG. 7 is a flowchart for the request routine in the third embodiment of the inventive method.

The request procedure for the embodiment of FIG. 4 is shown in FIG. 7. In this embodiment, a request is sent from the presentation unit PU to the implanted medical device IMD, and the implanted medical device runs the requested software, and transmits proper information back to the presentation unit PU, where it is displayed.

Figure 8:
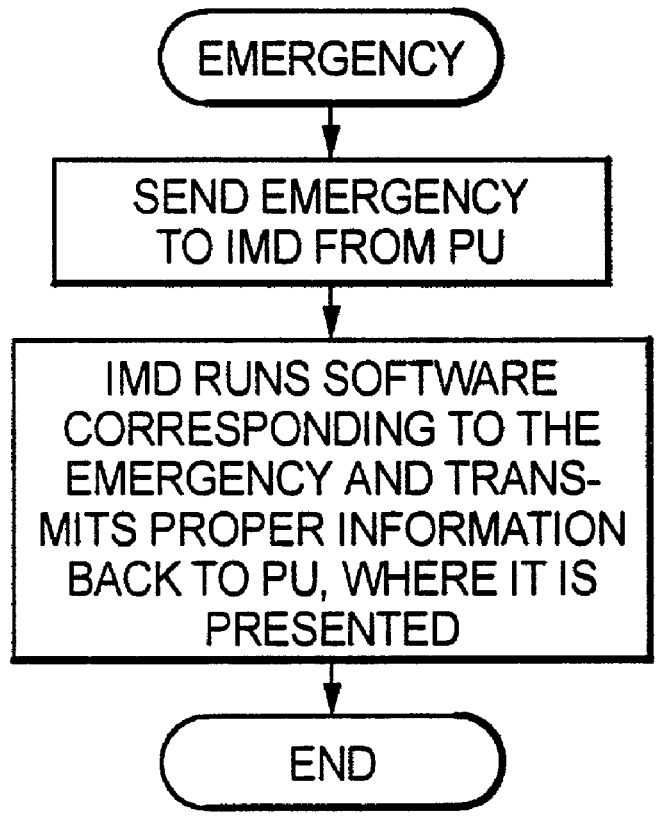
FIG. 8 is a flowchart for the emergency routine in all embodiments of the inventive method.

The emergency routine, which is applicable to all of the embodiments, is shown in FIG. 8. In this routine, an indication that an emergency exists is sent from the presentation unit PU to the implanted medical device IMD, and the implanted medical device IMD runs software responsive to the emergency, and transmits proper information back to the presentation unit, where the information is displayed. As noted above, this routine runs without any delay associated with a check for, or a download of, updated software, so that a response to the emergency can be initiated as quickly as possible.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for providing software to an implantable medical device system, comprising the steps of:
   providing an implantable medical device system having a plurality of system units each requiring software for the operation thereof, said system units including at least an implantable medical device and a presentation unit which are in communication with each other;
   storing a most current software version for operating each of said system units at a server remote from said implantable medical device system;

upon said start-up of said presentation unit, determining whether an entry has been made into said presentation unit indicating an emergency and, if so, immediately establishing communication between said presentation unit and said implanted medical device to respond to said emergency and, if not, establishing a communication link exclusively between said server and said presentation unit;

providing information to said server from said presentation unit via said communication link identifying software currently stored in at least one of said system units; and at said server, automatically determining whether said software stored in said at least one of said system units requires an update and, if so, downloading at least apportion of said software version stored at said server for receipt by said at least one of said system units.

2. A method as claimed in claim 1, wherein the step of downloading said software version comprises downloading said software directly from the server to said at least one of said system units.

3. A method as claimed in claim 1, wherein the step of downloading said software version comprises downloading said software version to said presentation unit and, if the system unit requiring an update is not said presentation unit, transmitting the software version from the presentation unit to the system unit requiring an update.

4. A method as claimed in claim 1 comprising permanently storing said software version, downloaded from said server, in said system unit requiring an update.

5. A method as claimed in claim 1 comprising temporarily storing said software version, downloaded from said server, in said system unit requiring an update, for a time period necessary to perform a task requiring said software version.

6. A method as claimed in claim 1 comprising establishing a further communication link directly between said server and said system unit requiring an update, if said system unit requiring an update is not said presentation unit, and directly downloading said software version from said server to said system unit requiring an update.

7. A method as claimed in claim 1 comprising, when establishing said communication link between said server and said presentation unit upon start-up of said presentation unit, communicating information from said presentation unit to said server identifying at least said implantable medical device.

8. A method as claimed in claim 7 comprising, when establishing said communication link between said server and said presentation unit upon start-up of said presentation unit, additionally supplying information from said presentation unit to said server identifying a user of said presentation unit.

9. A method as claimed in claim 8 comprising storing a plurality of most current versions of software for operating said system unit at said server, said current versions being respectively adapted to different users, and downloading one of said plurality of current versions of said software from said server dependent on said identification of said user.

10. A method as claimed in claim 1 wherein said software currently stored in said at least one of said system units comprises respectively different software portions respectively employed by said one of said system units for performing different tasks, and wherein the step of establishing a communication link includes informing said server of a task to be performed by said at least one of said system units, and wherein the step of downloading said software version at said server comprises downloading only a portion of said software stored at said server necessary for performing said task to be performed by said one of said system units.

11. A method as claimed in claim 1 wherein said software currently stored in said at least one of said system units comprises respectively different software portions respectively employed by said one of said system units for performing different routines, and wherein the step of establishing a communication link includes informing said server of a routine to be performed by said at least one of said system units, and wherein the step of downloading said software version at said server comprises downloading only a portion of said software stored at said server necessary for performing said routine to be performed by said one of said system units.

* * * * *